United States Patent [19]

Meyer et al.

[11] Patent Number: 4,478,635

[45] Date of Patent: Oct. 23, 1984

[54] N-ARYLSULFONYL-N'-PYRIMIDINYLUREAS

[75] Inventors: Willy Meyer, Riehen; Karl Gass, Magden; Werner Töpfl, Dornach; Rolf Schurter, Binningen, all of Switzerland; Georg Pissiotas, Lörrach, Fed. Rep. of Germany

[73] Assignee: Ciba-Geigy Corporation, Ardsley, N.Y.

[21] Appl. No.: 455,175

[22] Filed: Jan. 3, 1983

[30] Foreign Application Priority Data

Jan. 11, 1982 [CH] Switzerland ............ 124/82

[51] Int. Cl.³ .............. C07D 239/69; A01N 43/54
[52] U.S. Cl. ................................. 71/92; 544/321
[58] Field of Search ................... 544/321; 71/92

[56] References Cited

U.S. PATENT DOCUMENTS 4,214,890 7/1980 Levitt ........................ 71/90
4,383,113 5/1983 Levitt ........................ 544/211

FOREIGN PATENT DOCUMENTS 0009419 4/1980 European Pat. Off. .
0030141 6/1981 European Pat. Off. .

*Primary Examiner*—Robert Gerstl
*Attorney, Agent, or Firm*—Frederick H. Rabin

[57] ABSTRACT

The invention relates to N-arylsulfonyl-N'-pyrimidinyl ureas of the general formula

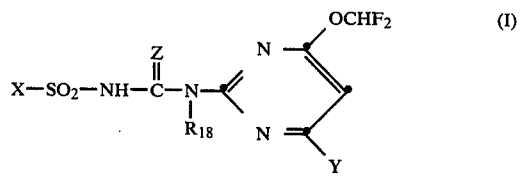

and to the salts thereof with amines, alkali metal hydroxides or alkaline earth metal hydroxides or with quaternary ammonium bases. These compounds have good pre- and postemergence selective herbicidal and growth regulating properties.

In the formula, $R_{18}$ is hydrogen, alkyl or alkoxy, X is an unsubstituted or substituted phenyl radical or an unsubstituted or substituted naphthyl radical, Y is $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_2$-$C_3$alkoxyalkyl, halogen or an unsubstituted amino group and Z is oxygen or sulfur.

25 Claims, No Drawings

N-ARYLSULFONYL-N'-PYRIMIDINYLUREAS

The present invention relates to novel N-arylsulfonyl-N'-pyrimidinylureas with herbicidal and plant growth regulating properties, to the preparation thereof, to compositions containing them, and to the use of these novel compounds for controlling weeds, in particular selectively, in crops of useful plants, or for regulating and inhibiting plant growth. The invention further relates to novel aminopyridines prepared as intermediates.

The N-arylsulfonyl-N'-pyrimidinylureas of this invention, and salts thereof, have the general formula I

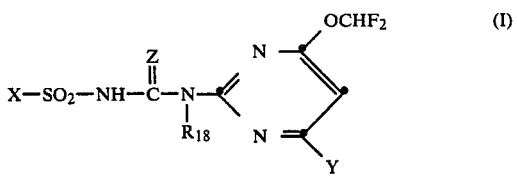

wherein
X is a radical of the formula

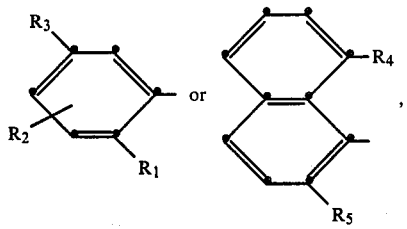

Y is $C_1$-$C_3$alkyl, $C_1$-$C_3$haloalkyl, $C_1$-$C_3$alkoxy, $C_1$-$C_3$haloalkoxy, $C_2$-$C_3$alkoxyalkyl, $C_1$-$C_3$alkylthio, halogen or —$NR_{16}R_{17}$,
Z is oxygen or sulfur,
$R_1$ is hydrogen, halogen, cyano, nitro, $C_1$-$C_4$haloalkyl, $C_1$-$C_4$alkyl, $C_1$-$C_4$alkoxy, —CO—$R_6$, —$NR_7R_8$, —$S(O)_m$—$C_1$-$C_4$alkyl or —$SO_2R_9$,
$R_2$ is hydrogen, fluorine, chlorine, bromine, nitro, trifluoromethyl, —$NR_{20}R_{21}$, methyl, ethyl, methoxy, ethoxy or —$S(O)_m$—$C_1$-$C_4$alkyl,
$R_3$ is hydrogen, fluorine, chlorine, bromine, amino, nitro or methoxy,
$R_6$ is hydrogen, $C_1$-$C_4$alkyl, $C_3$-$C_5$alkenyloxy, $C_3$-$C_5$alkynyloxy, $C_1$-$C_4$haloalkyl, $C_1$-$C_5$alkylthio, phenoxy, benzyloxy, —$NR_{10}R_{11}$ or $C_1$-$C_5$alkoxy which is unsubstituted or substituted by 1 to 3 halogen atoms or $C_1$-$C_3$alkoxy,
$R_7$ is hydrogen, methoxy, ethoxy, $C_1$-$C_4$alkyl or —CO—$R_{12}$,
$R_8$ is hydrogen or $C_1$-$C_4$alkyl,
$R_9$ is an —O—$R_{13}$ or —$NR_{14}R_{15}$ group,
$R_{13}$ is $C_1$-$C_4$alkyl which is unsubstituted or substituted by 1 to 3 halogen atoms, or is phenyl or benzyl,
$R_{18}$ is hydrogen, $C_1$-$C_3$alkyl or $C_1$-$C_3$alkoxy, and
m is 0, 1 or 2,
and $R_4$ has the same meaning as $R_2$; $R_5$ has the same meaning as $R_1$; $R_{10}$, $R_{11}$, $R_{14}$ and $R_{20}$ have each the same meaning as $R_7$; and $R_{12}$, $R_{15}$, $R_{16}$, $R_{17}$ and $R_{21}$ have each the same meaning as $R_8$.

Ureas, triazines and pyrimidines with herbicidal properties are generally known. Recently, arylsulfamoyl heterocyclylaminocarbamoyl compounds with herbicidal and plant growth regulating properties have been described e.g. in European published patent specification Nos. 9419 and 30141.

In the definitions of the substituents above, alkyl will be understood as meaning straight chain or branched alkyl, e.g. methyl, ethyl, n-propyl, isopropyl or the 4 butyl isomers. Alkoxy is methoxy, ethoxy, n-propoxy, isopropoxy, the 4 butoxy isomers, n-amyloxy, isoamyloxy, 2-amyloxy or 3-amyloxy, with methoxy, ethoxy or isopropoxy being preferred.

Alkylthio is e.g. methylthio, ethylthio, n-propylthio, isopropylthio, n-butylthio or n-pentylthio, with methylthio and ethylthio being preferred.

Examples of alkenyl radicals are vinyl, allyl, isopropenyl, propen-1-yl, buten-1-yl, buten-2-yl, buten-3-yl, isobuten-1-yl, isobuten-2-yl, penten-1-yl, penten-2-yl, penten-3-yl and penten-4-yl, with vinyl, allyl and penten-4-yl being preferred.

Alkylsulfinyl is e.g. methylsulfinyl, ethylsulfinyl, n-propylsulfinyl and n-butylsulfinyl, with methylsulfinyl and ethylsulfinyl being preferred.

Alkylsulfonyl is e.g. methylsulfonyl, ethylsulfonyl or n-propylsulfonyl, with methylsulfonyl and ethylsulfonyl being preferred.

Halogen by itself and as moiety of haloalkoxy is fluorine, chlorine and bromine, with fluorine and chlorine being preferred.

Alkynyl radicals in the definitions of the above symbols will normally be propargyl, butyn-2-yl, butyn-3-yl as well as pentynyl radicals. Preferably, however, alkynyl is propargyl or butyn-2- or -3-yl.

The invention also relates to the salts which the compounds of the formula I are able to form with amines, alkali metal bases and alkaline earth metal bases, or with quaternary ammonium bases.

The alkali metal hydroxides and alkaline earth metal hydroxides preferably used as salt formers are the hydroxides of lithium, sodium, potassium, magnesium or calcium, with sodium or potassium hydroxide being particularly preferred.

Examples of suitable salt-forming amines are primary, secondary and tertiary aliphatic and aromatic amines such as methylamine, ethylamine, propylamine, isopropylamine, the 4 isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine and triethylamine, with isopropylamine and diethanolamine being most preferred.

Examples of quaternary ammonium bases are in general the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those of the narrower subformula Ia

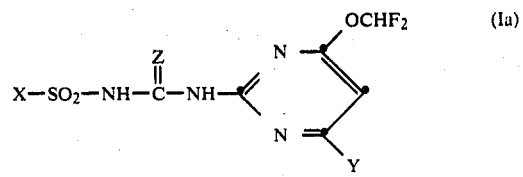

wherein
X is a radical of the formula

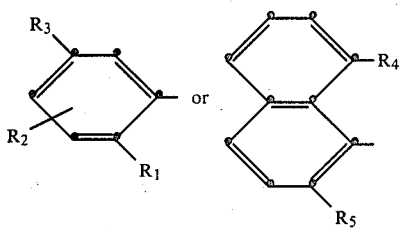

Y is methyl, ethyl, methoxy, ethoxy, difluoromethoxy, dimethylamino, or ethylmethylamino, Z is oxygen or sulfur, $R_1$ is hydrogen, fluorine, chlorine, bromine, iodine, cyano, nitro, trifluoromethyl, $C_1$-$C_4$alkyl, $C_1$-$C_4$alkoxy, —CO—$R_6$, —$NR_7R_8$, —$S(O)_m$—$C_1$-$C_4$alkyl or —$SO_2$—$R_9$, $R_2$ is hydrogen, fluorine, chlorine, bromine, nitro, trifluoromethyl, amino, methyl, ethyl, methoxy, ethoxy or —$S(O)_m$—$C_1$-$C_3$alkyl, $R_3$ is hydrogen, fluorine, chlorine, bromine, nitro or methoxy, $R_6$ is hydrogen, $C_1$-$C_3$alkyl, $C_3$-$C_5$alkenyloxy, $C_3$-$C_5$alkynyloxy, $C_1$-$C_5$alkylthio, phenoxy, benzyloxy, —$NR_{10}R_{11}$ or $C_1$-$C_5$alkoxy which is unsubstituted or substituted by 1 to 3 halogen atoms, $R_7$ is hydrogen, methoxy, ethoxy, $C_1$-$C_4$alkyl or —CO—$R_{12}$, $R_8$ is hydrogen or $C_1$-$C_4$alkyl, $R_9$ is an —O—$R_{13}$ or —$NR_{14}R_{15}$ group, $R_{13}$ is $C_1$-$C_4$alkyl, phenyl or benzyl and m is 0, 1 or 2, and $R_4$ has the same meaning as $R_2$; $R_5$ has the same meaning as $R_1$; $R_{10}$ and $R_{14}$ have each the same meaning as $R_7$; and $R_{11}$, $R_{12}$ and $R_{15}$ have each the same meaning as $R_8$, and the salts thereof.

Preferred compounds of the formulae I and Ia are those in which (a) X is the unsubstituted or substituted phenyl radical,
(b) Y is a radical containing at most 2 carbon atoms,
(c) Z is oxygen,
(d) $R_3$ and $R_4$ are hydrogen and
(e) $R_{18}$ is hydrogen or methyl.

Combining a number of preferred features results in further preferred groups of compounds of the formulae I and Ia in which X is the unsubstituted or substituted phenyl radical, Y is a radical containing at most 2 carbon atoms, Z is oxygen, and $R_3$ and $R_{18}$ are hydrogen. Within this group of compounds, those compounds are further preferred in which $R_2$ is hydrogen.

A particularly preferred subgroup of compounds of the formula I comprises those compounds in which X is the unsubstituted or substituted phenyl nucleus, Y is a radical containing at most 2 carbon atoms, Z is oxygen and $R_{18}$ is hydrogen, and wherein $R_1$ is hydrogen, halogen, nitro, $C_1$-$C_4$haloalkyl, $C_1$-$C_4$alkoxy, $C_1$-$C_4$alkyl, —$S(O)_m$—$C_1$-$C_4$alkyl, —$SO_2$—$N(CH_3)_2$, —SO—$OCH_2CF_3$ or —CO—$R_6$; $R_2$ is hydrogen, fluorine, chlorine, nitro, amino, trifluoromethyl, methyl, methoxy, ethoxy or —$S(O)_m$—$C_1$-$C_4$alkyl, $R_6$ is hydrogen, methyl, $C_3$-$C_5$alkenyloxy, $C_3$-$C_5$alkynyloxy, $C_1$-$C_3$alkylthio, dimethylamino, methylamino, amino, or $C_1$-$C_5$alkoxy which is unsubstituted or substituted by 1 to 3 halogen atoms or $C_1$-$C_3$alkoxy; and m is 0,1 or 2.

Preferred individual compounds are:

N-(2-chlorophenylsulfonyl)-N'-(4-difluoromethoxy-6-methylpyrimidin-2-yl)urea,

N-(2-methoxycarbonylphenylsulfonyl)-N'-(4-difluoromethoxy-6-methoxypyrimidine-2-yl)urea, N-(2-nitrophenylsulfonyl)-N'-(4-difluoromethoxy-6-methylpyrimidin-2-yl)urea, N-(2-methoxycarbonylphenylsulfonyl)-N'-[4,6-bis-(difluoromethoxy)pyrimidin-2-yl]urea and N-(2-methoxycarbonylphenylsulfonyl)-N'-(4-difluoromethoxy-6-methylpyrimidin-2-yl)urea.

The preparation of the compounds of formula I is carried out in an inert organic solvent.

In a first process, the compounds of formula I are obtained by reacting an arylsulfonamide of the formula II

wherein X is as defined for formula I, with a N-pyrimidinylcarbamate of the formula III

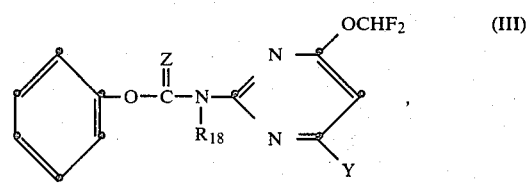

wherein $R_{18}$, Y and Z are as defined for formula I, in the presence of a base.

In a second process, the compounds of formula I are obtained by reacting an arylsulfonylisocyanate or arylsulfonylisothiocyanate of the formula

wherein X and Z are as defined for formula I, with an aminopyrimidine of the formula V

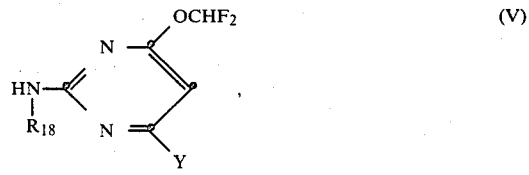

wherein $R_{18}$ and Y are as defined for formula I, optionally in the presence of a base.

In a further process, the compounds of formula I, wherein $R_{18}$ is hydrogen, are prepared by reacting an arylsulfonamide of the formula II above with an isocyanate or isothiocyanate of the formula VI

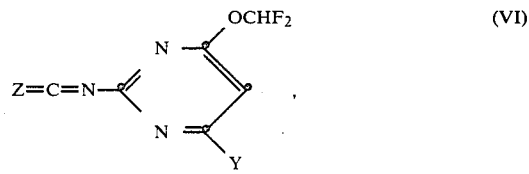

wherein Y and Z are as defined for formula I, optionally in the presence of a base.

Finally, the compounds of formula I may also be obtained by reacting an N-arylsulfonylcarbamate of the formula VII

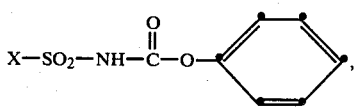

wherein X is as defined for formula I, with an aminopyridine of the formula V above.

If desired, the ureas of the formula I may be converted into addition salts with amines, alkali metal hydroxides or alkaline earth metal hydroxides, or with quaternary ammonium bases. This conversion is carried out by reaction with an equimolar amount of base and evaporation of the solvent.

These reactions to obtain compounds of the formula I are conveniently conducted in aprotic, inert organic solvents such as methylene chloride, tetrahydrofuran, acetonitrile, dioxan or toluene.

The reaction temperatures are preferably in the range from $-20°$ to $+120°$ C. The reactions are usually slightly exothermic and can be carried out at room temperature. To shorten the reaction time or also to initiate the reaction, it is expedient to heat the reaction mixture briefly to boiling point. The reaction times can also be shortened by adding a few drops of base or isocyanate as catalyst.

As suitable bases there may be used both organic bases such as amines, e.g. triethylamine, quinuclidine, pyridine, etc., and inorganic bases such as hydrides, e.g. sodium or calcium hydride, hydroxides such as sodium and potassium hydroxide, carbonates such as sodium and potassium carbonate, or bicarbonates such as potassium and sodium bicarbonate.

The final products can be isolated by concentrating the reaction mixture and/or evaporating the solvent, and purified by recrystallising or triturating the solid residue in solvents in which they are reluctantly soluble, such as ethers, aromatic hydrocarbons or chlorinated hydrocarbons.

The compounds of formula I are stable compounds and no precautionary measures are required for handling them.

The intermediates of the formulae II, IV and VII are known or they may be prepared by methods similar to known ones.

Some of the intermediates of the formula V are disclosed in European patent application No. 82810300.2. The novel starting compounds of this type have the general formula Va

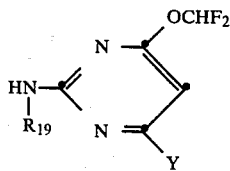

wherein Y is as defined for formula I and $R_{19}$ is $C_1$-$C_3$alkyl or $C_1$-$C_3$alkoxy. These novel intermediates have been specially developed for the synthesis of the compounds of formula I and therefore also constitute a further object of the invention.

The compounds of the formula Va are obtained by reacting an aminopyrimidine of the formula VIII

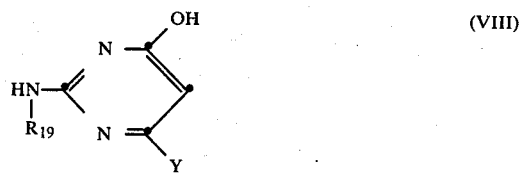

wherein Y is as defined for formula I and $R_{19}$ is $C_1$-$C_3$alkyl or $C_1$-$C_3$alkoxy, with difluorochloromethane or difluorobromomethane, in the presence of a base.

The process for the preparation of the compounds of formula Va is conveniently carried out in an inert polar solvent or mixture of solvents. Suitable solvents are ethers such as dioxan, tetrahydrofuran, ethylene glycol dimethyl ether or diethylene glycol dimethyl ether; alcohols such as methanol or ethanol; ketones such as acetone or ethylene methyl ketone; dimethylformamide; acetonitrile or dimethylsulfoxide. Particularly suitable bases are: sodium and calcium hydride, potassium and sodium hydroxide, potassium and sodium carbonate. In suitable cases, the base may be used in the form of an aqueous solution.

The starting materials of the formula VIII are known or they are prepared by methods similar to known ones.

Some of the intermediates of the formulae III and VI are known from European patent application No. 82810300.2 or they are prepared from the intermediates of formula V by methods similar to known ones.

When used in lower rates of application, the compounds of formula I have good selective growth-inhibiting and selective herbicidal properties which make them most suitable for use in crops of useful plants, especially in sugar cane, cereals, cotton, soybeans, maize and rice. In some cases damage is also caused to weeds which have up to now only been controlled with total herbicides.

The mode of action of these compounds is unusual. Many are translocatable, i.e. they are absorbed by the plant and transported to other parts of it where they then exert their action. Accordingly, for example, it is possible to damage perennial weeds to their roots by surface treatment. Compared with other herbicides and growth regulators, the novel compounds of formula I are effective even when used in very low rates of application.

The compounds of formula I have moreover pronounced plant growth regulating properties which can result in an increase in yield of cultivated plants or harvested products. In addition, many compounds of formula I have a growth inhibiting action which is dependent on the concentration employed. Both monocot and dicot plants are inhibited in their growth.

Thus, for example, the compounds of formula I selectively inhibit the growth of leguminosae which are frequently planted as cover crops in tropical regions, so that while soil erosion between cultivated plants is prevented, the cover crops cannot compete with the cultivated plants.

In many cultivated plants, inhibition of vegetative growth permits more plants to be sown in a crop area, so that a higher yield may be obtained per unit of area. A further mechanism of yield increase using growth regulators resides in the feature that nutrients are increasingly able to promote flower formation and fruiting, whilst vegetative growth is restricted.

It is sometimes desirable and advantageous to inhibit the vegetative growth of monocot plants, e.g. grasses or also cultivated plants such as cereals. Such a growth inhibition is of economic interest, inter alia, in respect of grasses, as the frequency of cutting in flower gardens, parks, sports fields or road shoulders can thereby be reduced. Of importance too is the inhibition of growth of herbaceous and ligneous plants on road shoulders and near transmission lines, or generally in areas in which strong growth is undesirable.

The use of growth regulators for inhibiting the growth in height of cereals is also important, as shortening the stalks diminishes or completely eliminates the danger of lodging before harvesting. In addition, growth regulators are able to effect a strengthening of the stalks in crops of cereals and this response too counteracts lodging.

Further, the compounds of formula I are suitable for preventing stored potatoes from sprouting. During winter storage, potatoes often develop sprouts, resulting in shrinkage, weight loss and rot. At higher rates of application, all tested plants are so damaged in their development that they wither and die.

The invention also relates to herbicidal and plant growth regulating compositions which contain a novel compound of formula I, and also to methods of controlling weeds pre- and postemergence and of inhibiting the growth of monocots and dicots, especially grasses, tropical cover plants and tobacco plant suckers.

The compounds of the formula I are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$ alkyl radical which also includes the alkyl moiety of acyl radicals, e.g. the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide. The surfactants customarily employed in the art of formulation are described e.g. in "McCutcheon's Detergents and Emulsifiers Annual", MC Publishing Corp. Ringwood, N.J., 1979, and Sisely and Wood, "Encyclopedia of Surface Active Agents", Chemical Publishing Co., Inc. New York, 1980.

The pesticidal compositions usually contain 0.1 to 95%, preferably 0.1 to 80%, of a compound of the formula I, 1 to 99.9% of a solid or liquid adjuvant, and 0 to 25%, preferably 0.1 to 25%, of a surfactant.

Preferred formulations are composed in particular of the following constituents (%=percentage by weight):

| Emulsifiable concentrates | |
| --- | --- |
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001%. The rates of application are normally 0.01 to 10 kg a.i./ha, preferably 0.025 to 5 kg a.i./ha.

The compositions can also contain further ingredients such as stabilisers, antifoams, viscosity regulators, binders, adhesives, as well as fertilisers or other active compounds, in order to attain special effects.

PREPARATORY EXAMPLES

EXAMPLE 1

N-(2-Chlorphenylsulfonyl)-N'-(4-difluoromethoxy-6-methylpyrimidin-2-yl)urea

A solution of 4.9 g (0.0225 mole) of 2-chlorophenylsulfonyl isocyanate and 3.5 g (0.02 mole) of 2-amino-4-difluoromethoxy-6-methylpyrimidine in 70 ml of dioxan is stirred for 2 hours at 60°–70° C. The reaction mixture is filtered and the filtrate is concentrated. The residue is triturated with ether to give 3.8 g (49.9% of theory) of N-(2-chlorophenylsulfonyl)-N'-(4-difluoromethoxy-6-methylpyridin-2-yl)urea with a melting point of 169°–170° C.

EXAMPLE 2

N-(2-Methoxycarbonylphenylsulfonyl)-N'-[4,6-bis-(difluoromethoxy)pyrimidin-2-yl]urea 3.62 g (0.0158 mole) of 2-methoxycarbonylphenylsulfonylisocyanate and 2.63 g (0.0116 mole) of 2-amino-4,6-bis-(difluoromethoxy)pyrimidine are reacted in 50 ml of dioxan as described in Example 1, affording the title compound with a melting point of 186°–188° C.

EXAMPLE 3

N-(2-Methoxycarbonylphenylsulfonyl)-N'-[4,6-bis-(difluoromethoxy)pyrimidin-2-yl]-N'-methylurea (a) 67.5 g (1 mole) of methylammonium chloride and 42 g (0.5 mole) of cyanoguanidine are heated to 175° C. to give a clear colourless melt. After onset of reaction, the heat of reaction causes the temperature of the reaction mixture to rise to 206° C. The batch is then stirred for 3½ hours at 175° C., cooled to 80° C., diluted with 320 ml of methanol and then 172.3 g (0.97 mole) of a 30% solution of sodium methylate in methanol are added over 5 minutes. The resultant suspension is refluxed for 30 minutes and then 173 g (1.08 mole) of diethyl malonate are added over 5 minutes. This suspension is refluxed for another 6 hours and then diluted with 1.25 liters of water. The product is precipitated by acidifying the clear orange solution with glacial acetic acid to pH 4.5. The precipitate is isolated, washed with water and dried in vacuo over phosphorus pentoxide, affording 35.3 g (25% of theory) of 2-methylamino-4,6-dihydroxypyrimidine with a melting point of 290° C.

(b) A mixture of 35.3 g (0.25 mole) of 2-methylamino-4,6-dihydroxypyrimidine, 340 g (2.5 moles) of 30% aqueous sodium hydroxide solution and 600 ml of dioxan is heated to 75° C. Gaseous difluoromethane is then introduced into the resultant emulsion over 1½ hours. The organic phase is separated and concentrated. The residue is washed with ice water and dried, affording the desired 2-methylamino-4,6-bis-(difluoromethoxy)pyrimidine with a melting point of 54°–55° C.

(c) In the same manner as described in Example 1, 4.6 g (95.8% of theory) of N-(2-methoxycarbonylphenylsulfonyl)-N'-[4,6-bis-(difluoromethoxy)pyrimidin-2-yl]-N'-methylurea are obtained from 2.6 g (0.011 mole) of 2-methoxycarbonylphenylsulfonylisocyanate and 2.4 g (0.01 mole) of 2-methylamino-4,6-bis-(difluoromethoxy)pyrimidine in 30 ml of methylene chloride. The product melts at 114°–115° C. after recrystallisation from a mixture of acetone/ether.

The compounds listed in the following tables are obtained in corresponding manner.

TABLE 1

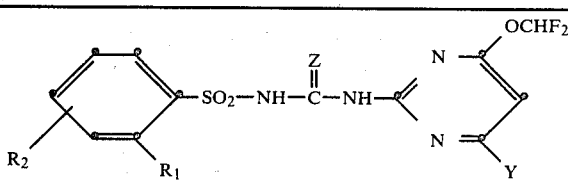

| Compound | R₁ | R₂ | Y | Z | m.p. |
|---|---|---|---|---|---|
| 1.1 | —COOCH₃ | H | CH₃ | O | 163–164° C. |
| 1.2 | —COOCH₃ | H | —OCHF₂ | O | 186–188° C. |
| 1.3 | —COOCH₃ | H | C₂H₅ | O | 170–171° C. |
| 1.4 | —COOCH₃ | H | OCH₃ | O | 177–178° C. |
| 1.5 | Cl | H | CH₃ | O | 169–170° C. |
| 1.6 | Cl | H | C₂H₅ | O | |
| 1.7 | Cl | H | —OCHF₂ | O | 181–182° C. |
| 1.8 | CH₃ | H | CH₃ | O | 168–171° C. |
| 1.9 | CH₃ | H | —OCHF₂ | O | |
| 1.10 | OCH₃ | H | CH₃ | O | 164–165° C. |
| 1.11 | OCH₃ | H | —OCHF₂ | O | 183–184° C. |
| 1.12 | OCH₃ | H | OCH₃ | O | 173–174° C. |
| 1.13 | CF₃ | H | OCHF₂ | O | |
| 1.14 | CF₃ | H | CH₃ | O | 203–204° C. (decomp.) |
| 1.15 | Br | H | —OCHF₂ | O | |
| 1.16 | Br | H | CH₃ | O | 170–171° C. |
| 1.17 | Br | H | C₂H₅ | O | |
| 1.18 | NO₂ | H | CH₃ | O | 194–195° C. (decomp.) |
| 1.19 | NO₂ | H | —OCHF₂ | O | 173–174° C. |
| 1.20 | NO₂ | H | OCH₃ | O | 182–184° C. |
| 1.21 | OCH₃ | 5-OCH₃ | CH₃ | O | 177–178° C. |
| 1.22 | OCH₃ | 5-OCH₃ | —OCHF₂ | O | |
| 1.23 | —CO—SCH₃ | H | —OCHF₂ | O | |
| 1.24 | —CO—SCH₃ | H | CH₃ | O | |
| 1.25 | —CO—N(CH₃)₂ | H | CH₃ | O | |
| 1.26 | —CO—N(CH₃)₂ | H | —OCHF₂ | O | |
| 1.27 | —CO—N(CH₃)₂ | H | —N(CH₃)₂ | O | |
| 1.28 | —CO—N(CH₃)OCH₃ | H | CH₃ | O | |
| 1.29 | —CO—N(CH₃)OCH₃ | H | —OCHF₂ | O | |
| 1.30 | —CHO | H | CH₃ | O | |
| 1.31 | —CHO | H | —OCHF₂ | O | |
| 1.32 | —CHO | H | C₂H₅ | O | |
| 1.33 | —SO₂—(CH₂)₂—CH₃ | H | CH₃ | O | 169–170° C. |
| 1.34 | —SO₂—(CH₂)₂—CH₃ | H | —OCHF₂ | O | |
| 1.35 | —SO₂—CH(CH₃)₂ | H | CH₃ | O | |
| 1.36 | —SO₂—CH(CH₃)₂ | H | —OCHF₂ | O | |
| 1.37 | —SO₂—CH(CH₃)₂ | H | OCH₃ | O | |
| 1.38 | —SO₂—CH(CH₃)₂ | H | —N(CH₃)₂ | O | |
| 1.39 | —SO₂—N(CH₃)₂ | 5-CF₃ | —OCHF₂ | O | |
| 1.40 | —SO₂—N(CH₃)₂ | 5-CF₃ | CH₃ | O | |
| 1.41 | —COOCH₃ | H | —N(CH₃)C₂H₅ | O | |
| 1.42 | Cl | H | —N(CH₃)₂ | O | 185–187° C. |
| 1.43 | NO₂ | H | —N(CH₃)₂ | O | 198–199° C. |
| 1.44 | OCH₃ | H | —N(CH₃)₂ | O | |
| 1.45 | CF₃ | H | —N(CH₃)₂ | O | |
| 1.46 | OCH₃ | 5-OCH₃ | —N(CH₃)₂ | O | |
| 1.47 | —CO—CH₃ | H | —N(CH₃)₂ | O | |
| 1.48 | NH₂ | H | —N(CH₃)₂ | O | |
| 1.49 | —COOCH₃ | 5-F | CH₃ | O | |
| 1.50 | —COOCH₃ | 5-F | —OCHF₂ | O | |
| 1.51 | —COOCH₃ | 5-F | —N(CH₃)₂ | O | |
| 1.52 | —COOCH₃ | 6-F | CH₃ | O | |
| 1.53 | —COOCH₃ | 6-F | —OCHF₂ | O | |
| 1.54 | —COOCH₃ | 6-F | —N(CH₃)₂ | O | 163–164° C. |
| 1.55 | OCH₃ | 6-Cl | CH₃ | O | |
| 1.56 | OCH₃ | 6-Cl | —OCHF₂ | O | |
| 1.57 | OCH₃ | 6-Cl | —N(CH₃)₂ | O | |
| 1.58 | —COOCH₃ | 5-Cl | CH₃ | O | |
| 1.59 | —COOCH₃ | 5-Cl | —OCHF₂ | O | |
| 1.60 | —COOCH₃ | 5-Cl | C₂H₅ | O | |
| 1.61 | NO₂ | H | CH₃ | S | |
| 1.62 | NO₂ | H | —OCHF₂ | S | |
| 1.63 | —SO₂—N(CH₃)₂ | H | CH₃ | S | |
| 1.64 | —SO₂—N(CH₃)₂ | H | —OCHF₂ | S | |
| 1.65 | —CO—CH₃ | H | CH₃ | S | |
| 1.66 | —CO—CH₃ | H | —OCHF₂ | S | |
| 1.67 | —COOCH(CH₃)₂ | H | CH₃ | O | 169–170° C. |
| 1.68 | —COOCH(CH₃)₂ | H | —OCHF₂ | O | |
| 1.69 | —COOCH(CH₃)₂ | H | OCH₃ | O | 178–180° C. |

TABLE 1-continued

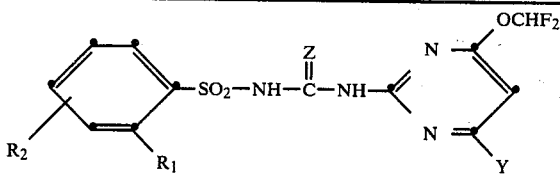

| Compound | R₁ | R₂ | Y | Z | m.p. |
|---|---|---|---|---|---|
| 1.70 | —COOCH₂—CH=CH₂ | H | CH₃ | O | |
| 1.71 | —COOCH₂—CH=CH₂ | H | —OCHF₂ | O | |
| 1.72 | —COOCH₂—CH=CH₂ | H | C₂H₅ | O | |
| 1.73 | —COOCH₂—CF₃ | H | CH₃ | O | |
| 1.74 | —COOCH₂—CF₃ | H | —OCHF₂ | O | |
| 1.75 | —COOCH₂—OCH₃ | H | CH₃ | O | |
| 1.76 | —COOCH₂—OCH₃ | H | —OCHF₂ | O | |
| 1.77 | —COOCH₃ | H | —OCH₂—CH₃ | O | 158–159° C. |
| 1.78 | —COOCH₃ | H | —N(CH₃)₂ | O | 229–230° C. |
| 1.79 | NH₂ | H | CH₃ | O | 222–225° C. (decomp.) |
| 1.80 | —NH—CO—CH₃ | H | CH₃ | O | 171–172° C. |
| 1.81 | NH₂ | H | —OCHF₂ | O | |
| 1.82 | —NH—CO—CH₃ | H | —OCHF₂ | O | |
| 1.83 | SCH₃ | H | CH₃ | O | 168–169° C. |
| 1.84 | SCH₃ | H | —OCHF₂ | O | 187–188° C. |
| 1.85 | —SO₂—CH₃ | H | CH₃ | O | 208° C. (decomp.) |
| 1.86 | —SO₂—CH₃ | H | —OCHF₂ | O | |
| 1.87 | CN | H | CH₃ | O | |
| 1.88 | CN | H | —OCHF₂ | O | |
| 1.89 | CN | H | OCH₃ | O | |
| 1.90 | —CO—CH₃ | H | CH₃ | O | |
| 1.91 | —CO—CH₃ | H | —OCHF₂ | O | |
| 1.92 | —CO—CH₃ | H | OCH₃ | O | |
| 1.93 | —SO₂—N(CH₃)₂ | H | CH₃ | O | 196–198° C. |
| 1.94 | —SO₂—N(CH₃)₂ | H | —OCHF₂ | O | 170–172° C. |
| 1.95 | F | H | CH₃ | O | 158–159° C. |
| 1.96 | F | H | —OCHF₂ | O | 200–201° C. |
| 1.97 | Cl | H | —OCHF₂ | S | 157–159° C. |
| 1.98 | Cl | H | CH₃ | S | 167° C. (decomp.) |
| 1.99 | —COOCH₃ | H | CHF₂ | O | |
| 1.100 | —COOCH₃ | H | CH₂F | O | 164–165° C. |
| 1.101 | —COOCH₃ | H | CF₃ | O | 165–166° C. |
| 1.102 | —COOCH₃ | H | Cl | O | 171–172° C. |
| 1.103 | —COOCH₃ | H | —OCH₂—CH₂F | O | |
| 1.104 | —COOCH₃ | H | —OCH₂—CF₃ | O | |
| 1.105 | —COOCH₃ | H | —NH—CH₃ | O | |
| 1.106 | —COOCH₃ | H | Br | O | |
| 1.107 | —COOCH₃ | H | CH₂Cl | O | |
| 1.108 | —COOCH₃ | H | F | O | |
| 1.109 | NO₂ | H | Cl | O | 190–191° C. |
| 1.110 | NO₂ | H | CF₃ | O | 175–176° C. |
| 1.111 | NO₂ | H | CH₂F | O | |
| 1.112 | NO₂ | H | CH₂Cl | O | |
| 1.113 | OCH₃ | H | Cl | O | 142–144° C. |
| 1.114 | OCH₃ | H | CF₃ | O | 153–154° C. |
| 1.115 | OCH₃ | H | CH₂F | O | |
| 1.116 | NH₂ | H | OCH₃ | O | |
| 1.117 | NH₂ | H | Cl | O | |
| 1.118 | Br | H | CH₂F | O | |
| 1.119 | Br | H | OCH₃ | O | |
| 1.120 | Br | H | —N(CH₃)₂ | O | |
| 1.121 | Br | H | Cl | O | |
| 1.122 | —COOCH₃ | 3-Cl | CH₃ | O | |
| 1.123 | —COOCH₃ | 3-Cl | OCH₃ | O | |
| 1.124 | —COOCH₃ | 3-Cl | OCHF₂ | O | |
| 1.125 | —COOCH₃ | 3-Cl | —N(CH₃)₂ | O | |
| 1.126 | —COOCH₃ | 3-F | CH₃ | O | |
| 1.127 | —COOCH₃ | 3-F | OCH₃ | O | |
| 1.128 | —COOCH₃ | 3-F | OCHF₂ | O | |
| 1.129 | —COOCH₃ | 3-F | —N(CH₃)₂ | O | |
| 1.130 | CH₃ | 6-Cl | CH₃ | O | 173–176° C. |
| 1.131 | CH₃ | 6-Cl | OCH₃ | O | |
| 1.132 | CH₃ | 6-Cl | OCHF₂ | O | |
| 1.133 | CH₃ | 6-Cl | —N(CH₃)₂ | O | |
| 1.134 | NO₂ | 3-Cl | CH₃ | O | |
| 1.135 | CH₃ | 6-CH₃ | CH₃ | O | |
| 1.136 | CH₃ | 6-CH₃ | OCH₃ | O | |
| 1.137 | —COOCH₃ | 6-CH₃ | CH₃ | O | |

TABLE 1-continued

Structure: phenyl(R1, R2)-SO2-NH-C(=Z)-NH-[pyrimidine with OCHF2 and Y substituents]

| Compound | R$_1$ | R$_2$ | Y | Z | m.p. |
|---|---|---|---|---|---|
| 1.138 | —COOCH$_3$ | 3-CH$_3$ | CH$_3$ | O | 173–175° C. (decomp.) |
| 1.139 | OCH$_3$ | H | C$_2$H$_5$ | O | |
| 1.140 | OCH$_3$ | 5-F | CH$_3$ | O | 173–175° C. (decomp.) |
| 1.141 | OCH$_3$ | 5-F | OCHF$_2$ | O | |
| 1.142 | OCH$_3$ | 5-F | OCH$_3$ | O | |
| 1.143 | OCH$_3$ | 5-F | —N(CH$_3$)$_2$ | O | |
| 1.144 | OCH$_3$ | 5-Cl | CH$_3$ | O | 176–177° C. (decomp.) |
| 1.145 | OCH$_3$ | 5-Cl | OCH$_3$ | O | |
| 1.146 | I | H | CH$_3$ | O | 164–166° C. |
| 1.147 | OCH$_3$ | H | C$_2$H$_5$ | O | 170–171° C. |
| 1.148 | H | H | CH$_3$ | O | 176–177° C. |
| 1.149 | Cl | H | OCH$_3$ | O | 172–173° C. |
| 1.150 | CH$_3$ | 5-NO$_2$ | CH$_3$ | O | 189–190° C. |
| 1.151 | CH$_3$ | 5-NH$_2$ | CH$_3$ | O | 133–135° C. |
| 1.152 | CH$_3$ | H | Cl | O | |
| 1.153 | CH$_3$ | H | OCH$_3$ | O | |
| 1.154 | CH$_3$ | H | —N(CH$_3$)$_2$ | O | |
| 1.155 | —NH—CO—CH$_3$ | H | OCH$_3$ | O | |
| 1.156 | OCH$_3$ | 5-OCH$_3$ | OCH$_3$ | O | |
| 1.157 | —CO—SCH$_3$ | H | OCH$_3$ | O | |
| 1.158 | —CO—SCH$_3$ | H | —N(CH$_3$) | O | |
| 1.159 | —CO—SCH$_3$ | H | Cl | O | |
| 1.160 | —CO—N(CH$_3$)$_2$ | H | OCH$_3$ | O | |
| 1.161 | —CO—N(CH$_3$)$_2$ | H | Cl | O | |
| 1.162 | —SO$_2$—C$_3$H$_7$—n | H | OCH$_3$ | O | |
| 1.163 | —SO$_2$—C$_3$H$_7$—n | H | —N(CH$_3$)$_2$ | O | |
| 1.164 | —SO$_2$—C$_3$H$_7$—n | H | Cl | O | |
| 1.165 | —SO$_2$—C$_3$H$_7$—n | H | Cl | O | |
| 1.166 | —SO$_2$—C$_2$H$_5$ | H | CH$_3$ | O | |
| 1.167 | —SO$_2$—C$_2$H$_5$ | H | —OCHF$_2$ | O | |
| 1.168 | —SO$_2$—C$_2$H$_5$ | H | OCH$_3$ | O | |
| 1.169 | —SO$_2$C$_2$H$_5$—n | H | —N(CH$_3$)$_2$ | O | |
| 1.170 | —SO$_2$C$_2$H$_5$ | H | Cl | O | |
| 1.171 | —SO$_2$—CH$_3$ | H | OCH$_3$ | O | |
| 1.172 | —SO$_2$—CH$_3$ | H | —N(CH$_3$)$_2$ | O | |
| 1.173 | —SO$_2$CH$_3$ | H | Cl | O | |
| 1.174 | Cl | H | Cl | O | |
| 1.175 | OCH$_3$ | 5-OCH$_3$ | Cl | O | |
| 1.176 | SCH$_3$ | H | OCH$_3$ | O | 181–182° C. |
| 1.177 | SCH$_3$ | H | Cl | O | |
| 1.178 | SCH$_3$ | H | —N(CH$_3$)$_2$ | O | |
| 1.179 | —SO$_2$—N(CH$_3$)$_2$ | H | OCH$_3$ | O | |
| 1.180 | —SO$_2$—N(CH$_3$)$_2$ | H | Cl | O | |
| 1.181 | —SO$_2$N(CH$_3$)$_2$ | H | —N(CH$_3$)$_2$ | O | |
| 1.182 | —COOCH$_3$ | 6-F | OCH$_3$ | O | |
| 1.183 | —CO—CH$_3$ | H | Cl | O | |
| 1.184 | —COOCH$_3$ | 6-F | Cl | O | |
| 1.185 | OCH$_3$ | 6-Cl | OCH$_3$ | O | |
| 1.186 | OCH$_3$ | 6-Cl | Cl | O | |
| 1.187 | —COOCH$_3$ | 5-Cl | OCH$_3$ | O | |
| 1.188 | —COOCH$_3$ | 5-Cl | Cl | O | |
| 1.189 | CN | H | —N(CH$_3$)$_2$ | O | |
| 1.190 | F | H | OCH$_3$ | O | 198–199° C. |
| 1.191 | F | H | —N(CH$_3$)$_2$ | O | |
| 1.192 | F | H | Cl | O | |
| 1.193 | I | H | OCHF$_2$ | O | 174–176° C. (decomp.) |
| 1.194 | I | H | OCH$_3$ | O | 134–136° C. (decomp.) |
| 1.195 | I | H | —N(CH$_3$)$_2$ | O | 234° C. (decomp.) |
| 1.196 | H | H | OCHF$_2$ | O | |
| 1.197 | H | H | OCH$_3$ | O | |
| 1.198 | H | H | —N(CH$_3$)$_2$ | O | |
| 1.199 | H | H | —N(CH$_3$)$_2$ | O | |
| 1.200 | NO$_2$ | 5-F | CH$_3$ | O | |
| 1.201 | NO$_2$ | 5-Cl | CH$_3$ | O | |
| 1.202 | OCH$_3$ | 6-SCH$_3$ | CH$_3$ | O | 140–143° C. |

TABLE 1-continued

[Structure: phenyl ring with R2 and R1 substituents, connected via -SO2-NH-C(=Z)-NH- to a pyrimidine ring bearing OCHF2 and Y substituents]

| Compound | R1 | R2 | Y | Z | m.p. |
|---|---|---|---|---|---|
| 1.203 | OCH$_3$ | 6-SCH$_3$ | OCH$_3$ | O | |
| 1.204 | OCH$_3$ | 6-SCH$_3$ | OCHF$_2$ | O | |
| 1.205 | —S—C$_3$H$_7$—i | H | CH$_3$ | O | |
| 1.206 | —S—C$_3$H$_7$—i | H | OCH$_3$ | O | |
| 1.207 | —S—C$_3$H$_7$—i | H | OCHF$_2$ | O | |
| 1.208 | —O—C$_2$H$_5$ | H | CH$_3$ | O | 188–189° C. |
| 1.209 | —O—C$_2$H$_5$ | H | OCH$_3$ | O | 172–173° C. |
| 1.210 | —O—C$_2$H$_5$ | H | OCHF$_2$ | O | 165–166° C. |
| 1.211 | —O—C$_2$H$_5$ | H | —N(CH$_3$)$_2$ | O | 195–196° C. |
| 1.212 | —O—C$_2$H$_5$ | H | Cl | O | |
| 1.213 | —C—C$_3$H$_7$—i | H | CH$_3$ | O | 166–167° C. |
| 1.214 | —O—C$_3$H$_7$—i | H | OCH$_3$ | O | 168–170° C. |
| 1.215 | —O—C$_3$H$_7$—i | H | OCHF$_2$ | O | 147–148° C. |
| 1.216 | —O—C$_3$H$_7$—i | H | —N(CH$_3$)$_2$ | O | |
| 1.217 | —O—C$_3$H$_7$—i | H | Cl | O | |
| 1.218 | —O—C$_3$H$_7$—n | H | CH$_3$ | O | |
| 1.219 | C$_2$H$_5$ | H | CH$_3$ | O | |
| 1.220 | C$_2$H$_5$ | H | OCH$_3$ | O | |
| 1.221 | C$_2$H$_5$ | H | OCHF$_2$ | O | |
| 1.222 | C$_2$H$_5$ | H | —N(CH$_3$)$_2$ | O | |
| 1.223 | C$_2$H$_5$ | H | Cl | O | |
| 1.224 | C$_2$H$_5$ | H | CH$_2$F | O | |
| 1.225 | C$_2$H$_5$ | H | CF$_3$ | O | |
| 1.226 | —COOCH$_3$ | H | —O—C$_3$H$_7$—i | O | |
| 1.227 | NO$_2$ | H | —O—C$_3$H$_7$—i | O | |
| 1.228 | NO$_2$ | H | —O—C$_2$H$_5$ | O | |
| 1.229 | NO$_2$ | H | —O—CH$_2$—CF$_3$ | O | |
| 1.230 | —COOCH$_3$ | H | —O—CH$_2$—CF$_3$ | O | |
| 1.231 | —COOCH$_3$ | H | SCH$_3$ | O | |
| 1.232 | NO$_2$ | H | SCH$_3$ | O | |
| 1.233 | CF$_3$ | H | SCH$_3$ | O | |
| 1.234 | —SO$_2$—N(CH$_3$)$_2$ | H | SCH$_3$ | O | |
| 1.235 | OCH$_3$ | H | SCH$_3$ | O | |
| 1.236 | —COOCH$_3$ | H | —CH$_2$—OCH$_3$ | O | |
| 1.237 | NO$_2$ | H | —CH$_2$—OCH$_3$ | O | |
| 1.238 | —COOCH$_3$ | H | —CH$_2$—OC$_2$H$_5$ | O | |
| 1.239 | NO$_2$ | H | —CH$_2$—OC$_2$H$_5$ | O | |
| 1.240 | —CH$_2$—CH$_2$—CF$_3$ | H | CH$_3$ | O | 164–165° C. |
| 1.241 | —CH$_2$—CH$_2$—CF$_3$ | H | OCH$_3$ | O | |
| 1.242 | —CH$_2$—CH$_2$—CF$_3$ | H | OCHF$_2$ | O | |
| 1.243 | —CH$_2$—CH$_2$—CF$_3$ | H | Cl | O | |
| 1.244 | —CH$_2$—CH$_2$CF$_3$ | H | —N(CH$_3$)$_2$ | O | |
| 1.245 | CF$_3$ | H | OCH$_3$ | O | |
| 1.246 | CF$_3$ | H | Cl | O | |
| 1.247 | CF$_3$ | H | —OC$_2$H$_5$ | O | |
| 1.248 | NH$_2$ | H | OCH$_3$ | O | |
| 1.249 | NH$_2$ | H | Cl | O | |
| 1.250 | —N(CH$_3$)$_2$ | H | CH$_3$ | O | 153–154° C. |
| 1.251 | —N(CH$_3$)$_2$ | H | OCH$_3$ | O | |
| 1.252 | —N(CH$_3$)$_2$ | H | OCHF$_2$ | O | |
| 1.253 | —N(CH$_3$)$_2$ | H | —N(CH$_3$)$_2$ | O | |
| 1.254 | —N(CH$_3$)$_2$ | H | Cl | O | |
| 1.255 | NO$_2$ | H | OCH$_3$ | S | |
| 1.256 | —CO—NH—CH$_3$ | H | CH$_3$ | O | |
| 1.257 | —CO—NH—CH$_3$ | H | OCH$_3$ | O | |
| 1.258 | —CO—NH—CH$_3$ | H | OCHF$_2$ | O | |
| 1.259 | —CO—NH$_2$ | H | CH$_3$ | O | |
| 1.260 | —CO—NH$_2$ | H | OCH$_3$ | O | |
| 1.261 | —CO—NH$_2$ | H | OCHF$_2$ | O | |
| 1.262 | CHO | H | OCH$_3$ | O | |
| 1.263 | CHO | H | —N(CH$_3$)$_2$ | O | |
| 1.264 | —CO—CF$_3$ | H | CH$_3$ | O | |
| 1.265 | —CO—CF$_3$ | H | OCH$_3$ | O | |
| 1.266 | —CO—CF$_3$ | H | OCHF$_2$ | O | |
| 1.267 | —SO—CH$_3$ | H | CH$_3$ | O | |
| 1.268 | —SO—CH$_3$ | H | OCH$_3$ | O | |
| 1.269 | —SO—CH$_3$ | H | OCHF$_2$ | O | |
| 1.270 | OCH$_3$ | H | —OC$_2$H$_5$ | O | |
| 1.271 | —OC$_3$H$_7$—n | H | OCH$_3$ | O | |
| 1.272 | —OC$_3$H$_7$—n | H | OCHF$_2$ | O | |
| 1.273 | —OC$_3$H$_7$—n | H | —N(CH$_3$)$_2$ | O | |

TABLE 1-continued

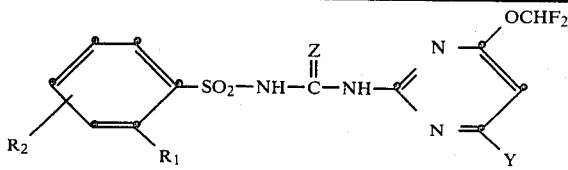

| Compound | $R_1$ | $R_2$ | Y | Z | m.p. |
|---|---|---|---|---|---|
| 1.274 | $-OC_3H_7-n$ | H | Cl | O | |
| 1.275 | $-OC_4H_9-n$ | H | $CH_3$ | O | |
| 1.276 | $-OC_4H_9-n$ | H | $OCH_3$ | O | |
| 1.277 | $-OC_4H_9-n$ | H | $OCHF_2$ | O | |
| 1.278 | $-COO-C_4H_9-s$ | H | $CH_3$ | O | 168–169° C. |
| 1.279 | $-COO-C_4H_9-s$ | H | $OCH_3$ | O | 164–166° C. |
| 1.280 | $-COO-C_4H_9-s$ | H | $OCHF_2$ | O | 167–169° C. |
| 1.281 | $-COO-CH(CH_3)CH_2-OCH_3$ | H | $CH_3$ | O | |
| 1.282 | $-COO-CH(CH_3)CH_2-OCH_3$ | H | $OCH_3$ | O | |
| 1.283 | $-COO-CH(CH_3)CH_2-OCH_3$ | H | $OCHF_2$ | O | |
| 1.284 | $-COO-C_4H_9-i$ | H | $CH_3$ | O | 125–130° C. |
| 1.285 | $-COO-C_4H_9-i$ | H | $OCH_3$ | O | 167–168° C. |
| 1.286 | $-COO-C_4H_9-i$ | H | $OCHF_2$ | O | |
| 1.287 | $-COO-C_5H_{11}-n$ | H | $CH_3$ | O | |
| 1.288 | $-COO-C_5H_{11}-n$ | H | $OCH_3$ | O | |
| 1.289 | $-COO-C_5H_{11}-n$ | H | $OCHF_2$ | O | |
| 1.290 | $-COO-CH_2-CH=CH_2$ | H | $OCH_3$ | O | |
| 1.291 | $-COO-CH_2-CF_3$ | H | $OCH_3$ | O | |
| 1.292 | $-COO-CH_2-C_6H_5$ | H | $CH_3$ | O | |
| 1.293 | $-COO-CH_2-C_6H_5$ | H | $OCH_3$ | O | |
| 1.294 | $-COO-CH_2-C_6H_5$ | H | $OCHF_2$ | O | |
| 1.295 | $-COO-CH_2-C\equiv CH$ | H | $CH_3$ | O | |
| 1.296 | $-COO-CH_2-C\equiv CH$ | H | $OCH_3$ | O | |
| 1.297 | $-COO-CH_2-C\equiv CH$ | H | $OCHF_2$ | O | |
| 1.298 | $-COO-CH_3$ | H | $CH_3$ | S | |
| 1.299 | $-COO-CH_3$ | H | $OCH_3$ | S | |
| 1.300 | $-COO-CH_3$ | H | $OCHF_2$ | S | |
| 1.301 | $-COO-CH_3$ | H | $-N(CH_3)_2$ | S | |
| 1.302 | $-COO-CH_3$ | H | $-CH_2Cl$ | O | |
| 1.303 | $-COO-CH_3$ | 6-Cl | $CH_3$ | O | |
| 1.304 | $-COO-CH_3$ | 6-Cl | $OCH_3$ | O | |
| 1.305 | $-COO-CH_3$ | 6-Cl | $OCHF_2$ | O | |
| 1.306 | $-COO-CH_3$ | 6-Cl | $-N(CH_3)_2$ | O | |
| 1.307 | $-COO-CH_3$ | 6-Cl | Cl | O | |
| 1.308 | $-COO-CH_3$ | 6-Cl | $CH_2F$ | O | |
| 1.309 | $-COO-CH_3$ | 6-Cl | $-OC_2H_5$ | O | |
| 1.310 | $-COO-C_2H_5$ | H | $CH_3$ | O | 150–152° C. |
| 1.311 | $-COO-C_2H_5$ | H | $OCH_3$ | O | |
| 1.312 | $-COO-C_2H_5$ | H | $OCHF_2$ | O | |
| 1.313 | $-COO-C_2H_5$ | H | $-N(CH_3)_2$ | O | |
| 1.314 | $-COO-C_2H_5$ | H | Cl | O | |
| 1.315 | $-COO-C_2H_5$ | H | $CH_2F$ | O | |
| 1.316 | $-COO-C_3H_7-i$ | H | $-N(CH_3)_2$ | O | |
| 1.317 | $-COO-CH_2CH_2-OCH_3$ | H | $CH_3$ | O | 150–152° C. |
| 1.318 | $-COO-CH_2CH_2-OCH_3$ | H | $OCH_3$ | O | |
| 1.319 | $-COO-CH_2CH_2-OCH_3$ | H | $OCHF_2$ | O | |
| 1.320 | $-COO-CH_2CH_2-OCH_3$ | H | $-N(CH_3)_2$ | O | |
| 1.321 | $-COO-CH_2CH_2-OCH_3$ | H | Cl | O | |
| 1.322 | $-COO-CH_2-CH_2-Cl$ | H | $CH_3$ | O | |
| 1.323 | $-COO-CH_2-Cl$ | H | $OCH_3$ | O | |
| 1.324 | $-COO-CH_2-CH_2-Cl$ | H | $OCHF_2$ | O | |
| 1.325 | $-COO-CH_2-CH_2-Cl$ | H | $-N(CH_3)_2$ | O | |
| 1.326 | $-COO-CH_2-CH_2-Cl$ | H | Cl | O | |
| 1.327 | $C_3H_7-n$ | H | $CH_3$ | O | 147–148° C. (decomp.) |
| 1.328 | $C_3H_7-n$ | H | $OCH_3$ | O | |
| 1.329 | $C_3H_7-n$ | H | $OCHF_2$ | O | |
| 1.330 | $C_3H_7-n$ | H | $-N(CH_3)_2$ | O | |
| 1.331 | $C_3H_7-n$ | H | Cl | O | |
| 1.332 | $C_3H_7-n$ | H | $CH_2F$ | O | |
| 1.333 | H | $3-NO_2$ | $CH_3$ | O | 190–193° C. |
| 1.334 | H | $3-NO_2$ | $OCH_3$ | O | |
| 1.335 | H | $3-NO_2$ | $OCHF_2$ | O | |
| 1.336 | $CH_2Cl$ | H | $CH_3$ | O | 153–156° C. |
| 1.337 | $CH_2Cl$ | H | $OCH_3$ | O | |
| 1.338 | $CH_2Cl$ | H | $OCHF_2$ | O | |
| 1.339 | $CH_2Cl$ | H | $-N(CH_3)_2$ | O | |
| 1.340 | $CH_2Cl$ | H | Cl | O | |
| 1.341 | $CH_2Cl$ | H | $CH_2F$ | O | |
| 1.342 | $-SO_2-O-CH_2CF_3$ | H | $CH_3$ | O | 176–179° C. |
| 1.343 | $-SO_2-O-CH_2-CF_3$ | H | $OCH_3$ | O | |

TABLE 1-continued

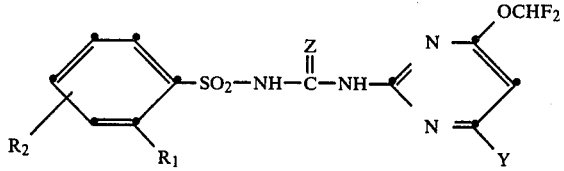

| Compound | R₁ | R₂ | Y | Z | m.p. |
|---|---|---|---|---|---|
| 1.344 | —SO₂—O—CH₂—CF₃ | H | OCHF₂ | O | |
| 1.345 | —SO₂—O—CH₂—CF₃ | H | —N(CH₃)₂ | O | |
| 1.346 | —SO₂—O—CH₂—CF₃ | H | Cl | O | |
| 1.347 | —SO₂—O—CH₂—CF₃ | H | CH₂F | O | |
| 1.348 | H | 3-COOCH₃ | CH₃ | O | |
| 1.349 | H | 3-COOCH₃ | OCH₃ | O | |
| 1.350 | H | 3-COOCH₃ | OCHF₂ | O | |
| 1.351 | H | 3-COOCH₃ | —N(CH₃)₂ | O | |
| 1.352 | OCH₃ | 4-NO₂ | CH₃ | O | 164–167° C. |
| 1.353 | OCH₃ | 4-NO₂ | OCH₃ | O | |
| 1.354 | OCH₃ | 4-NO₂ | OCHF₂ | O | |
| 1.355 | OCH₃ | 4-NO₂ | —N(CH₃)₂ | O | |
| 1.356 | OCH₃ | 4-NO₂ | Cl | O | |
| 1.357 | OCH₃ | 4-NH₂ | CH₃ | O | |
| 1.357 | OCH₃ | 4-NH₂ | OCH₃ | O | |
| 1.358 | OCH₃ | 4-NH₂ | OCH₃ | O | |
| 1.359 | OCH₃ | 4-NH₂ | OCHF₂ | O | |
| 1.360 | OCH₃ | 4-NH₂ | —N(CH₃)₂ | O | |
| 1.361 | OCH₃ | 4-NH₂ | Cl | O | |
| 1.362 | NH₂ | 6-OCH₃ | CH₃ | O | |
| 1.363 | NH₂ | 6-OCH₃ | OCH₃ | O | |
| 1.364 | NH₂ | 6-OCH₃ | OCHF₂ | O | |
| 1.365 | NH₂ | 6-OCH₃ | —N(CH₃)₂ | O | |
| 1.366 | NH₂ | 6-OCH₃ | Cl | O | |
| 1.367 | OCH₃ | 6-OCH₃ | CH₃ | O | |
| 1.368 | OCH₃ | 6-OCH₃ | OCH₃ | O | |
| 1.369 | OCH₃ | 6-OCH₃ | OCHF₂ | O | |
| 1.370 | OCH₃ | 6-OCH₃ | —N(CH₃)₂ | O | |
| 1.371 | OCH₃ | 6-OCH₃ | Cl | O | |
| 1.372 | OCH₃ | 3-OCH₃ | CH₃ | O | |
| 1.373 | OCH₃ | 3-OCH₃ | OCH₃ | O | |
| 1.374 | OCH₃ | 3-OCH₃ | OCHF₂ | O | |
| 1.375 | Cl | 6-Cl | CH₃ | O | 170–172° C. |
| 1.376 | Cl | 6-Cl | OCH₃ | O | |
| 1.377 | Cl | 6-Cl | OCHF₂ | O | |
| 1.378 | Cl | 6-Cl | —N(CH₃)₂ | O | |
| 1.379 | Cl | 6-Cl | Cl | O | |
| 1.380 | Cl | 6-Cl | CH₂F | O | |
| 1.381 | NO₂ | 6-Cl | CH₃ | O | 180° C. (decomp.) |
| 1.382 | NO₂ | 6-Cl | OCH₃ | O | 157° C. (decomp.) |
| 1.383 | NO₂ | 6-Cl | OCHF₂ | O | 175–177° C. (decomp.) |
| 1.384 | NO₂ | 6-Cl | —N(CH₃)₂ | O | 185–188° C. (decomp.) |
| 1.385 | NO₂ | 6-Cl | Cl | O | |
| 1.386 | NO₂ | 6-Cl | CH₂F | O | |
| 1.387 | Cl | 5-Cl | CH₃ | O | 207–209° C. |
| 1.388 | Cl | 5-Cl | OCH₃ | O | |
| 1.389 | Cl | 5-Cl | OCHF₂ | O | |
| 1.390 | OCH₃ | 5-CH₃ | CH₃ | O | 164–167° C. |
| 1.391 | OCH₃ | 5-CH₃ | OCH₃ | O | |
| 1.392 | OCH₃ | 5-CH₃ | OCHF₂ | O | |
| 1.393 | OCH₃ | 5-CH₃ | —N(CH₃)₂ | O | |
| 1.394 | OCH₃ | 5-CH₃ | Cl | O | |
| 1.395 | Cl | 3-Cl | CH₃ | O | 182–184° C. |
| 1.396 | Cl | 3-Cl | OCH₃ | O | |
| 1.397 | Cl | 3-Cl | OCHF₂ | O | |
| 1.398 | Cl | 3-Cl | —N(CH₃)₂ | O | |
| 1.399 | Cl | 3-Cl | Cl | O | |
| 1.400 | Cl | 3-Cl | CH₂F | O | |
| 1.401 | CH₃ | 5-NO₂ | CH₃ | O | 189–190° C. |
| 1.402 | CH₃ | 5-NO₂ | OCH₃ | O | |
| 1.403 | CH₃ | 5-NO₂ | OCHF₂ | O | |
| 1.404 | CH₃ | 5-NO₂ | —N(CH₃)₂ | O | |
| 1.405 | CH₃ | 5-NO₂ | Cl | O | |
| 1.406 | CH₃ | 5-NH₂ | CH₃ | O | 133–135° C. |
| 1.407 | CH₃ | 5-NH₂ | OCH₃ | O | |
| 1.408 | CH₃ | 5-NH₂ | OCHF₂ | O | |
| 1.409 | CH₃ | 5-NH₂ | —N(CH₃)₂ | O | |

TABLE 1-continued

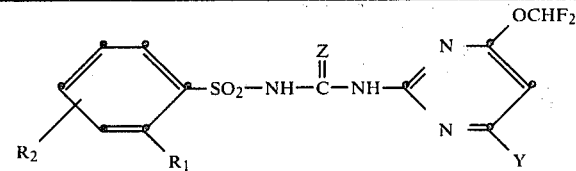

| Compound | $R_1$ | $R_2$ | Y | Z | m.p. |
|---|---|---|---|---|---|
| 1.410 | $CH_3$ | 5-$NH_2$ | Cl | O | |
| 1.411 | $NO_2$ | 6-$OCH_3$ | $CH_3$ | O | |
| 1.412 | $NO_2$ | 6-$OCH_3$ | $C_2H_5$ | O | |
| 1.413 | $NO_2$ | 6-$OCH_3$ | $CH_2F$ | O | |
| 1.414 | $NO_2$ | 6-$OCH_3$ | $CF_3$ | O | |
| 1.415 | $NO_2$ | 6-$OCH_3$ | $OCH_3$ | O | |
| 1.416 | $NO_2$ | 6-$OCH_3$ | $OC_2H_5$ | O | |
| 1.417 | $NO_2$ | 6-$OCH_3$ | $OCHF_2$ | O | |
| 1.418 | $NO_2$ | 6-$OCH_3$ | Cl | O | |
| 1.419 | $NO_2$ | 6-$OCH_3$ | —$(CH_3)_2$ | O | |
| 1.420 | $NO_2$ | 6-$OCH_3$ | $CH_3$ | S | |
| 1.421 | $NH_2$ | 6-Cl | $CH_3$ | O | 123° C. (decomp.) |
| 1.422 | $NH_2$ | 6-Cl | $C_2H_5$ | O | |
| 1.423 | $NH_2$ | 6-Cl | $CH_2F$ | O | |
| 1.424 | $NH_2$ | 6-Cl | $CF_3$ | O | |
| 1.425 | $NH_2$ | 6-Cl | $OCH_3$ | O | |
| 1.426 | $NH_2$ | 6-Cl | $OC_2H_5$ | O | |
| 1.427 | $NH_2$ | 6-Cl | $OCHF_2$ | O | |
| 1.428 | $NH_2$ | 6-Cl | Cl | O | |
| 1.429 | $NH_2$ | 6-Cl | —$N(CH_3)_2$ | O | |
| 1.430 | F | 6-Cl | $CH_3$ | O | |
| 1.431 | F | 6-Cl | $CH_2F$ | O | |
| 1.432 | F | 6-Cl | $CF_3$ | O | |
| 1.433 | F | 6-Cl | $OCH_3$ | O | |
| 1.434 | F | 6-Cl | $OCHF_2$ | O | |
| 1.435 | F | 6-Cl | Cl | O | |
| 1.436 | F | 6-Cl | —$N(CH_3)_2$ | O | |
| 1.437 | F | 6-Cl | $CH_3$ | S | |
| 1.438 | F | 6-Cl | $OCH_3$ | S | |
| 1.439 | F | 6-Cl | $OCHF_2$ | S | |
| 1.440 | F | 6-Cl | —$(CH_3)_2$ | S | |
| 1.441 | Br | 6-Cl | $CH_3$ | O | |
| 1.442 | Br | 6-Cl | $CH_2F$ | O | |
| 1.443 | Br | 6-Cl | $CF_3$ | O | |
| 1.444 | Br | 6-Cl | $OCH_3$ | O | |
| 1.445 | Br | 6-Cl | $OCHF_2$ | O | |
| 1.446 | Br | 6-Cl | Cl | O | |
| 1.447 | Br | 6-Cl | —$N(CH_3)_2$ | O | |
| 1.448 | I | 6-Cl | $CH_3$ | O | 129-131° C. (decomp.) |
| 1.449 | I | 6-Cl | $CH_2F$ | O | |
| 1.450 | I | 6-Cl | $CF_3$ | O | |
| 1.451 | I | 6-Cl | $OCH_3$ | O | |
| 1.452 | I | 6-Cl | $OCHF_2$ | O | 138° C. (decomp.) |
| 1.453 | I | 6-Cl | —$N(CH_3)_2$ | O | |
| 1.454 | I | 6-Cl | $CH_3$ | S | |
| 1.455 | Br | 6-Cl | $CH_3$ | S | |
| 1.456 | —$COOCH_3$ | 6-$CH_3$ | $C_2H_5$ | O | |
| 1.457 | —$COOCH_3$ | 6-$CH_3$ | $CH_2F$ | O | |
| 1.458 | —$COOCH_3$ | 6-$CH_3$ | $CF_3$ | O | |
| 1.459 | —$COOCH_3$ | 6-$CH_3$ | $OCH_3$ | O | |
| 1.460 | —$COOCH_3$ | 6-$CH_3$ | $OCHF_2$ | O | |
| 1.461 | —$COOCH_3$ | 6-$CH_3$ | Cl | O | |
| 1.462 | —$COOCH_3$ | 6-$CH_3$ | $OC_2H_5$ | O | |
| 1.463 | —$COOCH_3$ | 6-$CH_3$ | —$N(CH_3)_2$ | O | |
| 1.464 | —$COO-C_2H_5$ | 6-$CH_3$ | $CH_3$ | O | |
| 1.465 | —$COO-C_2H_5$ | 6-$CH_3$ | $OCH_3$ | O | |
| 1.466 | —$COO-C_2H_5$ | 6-$CH_3$ | $OCHF_2$ | O | |
| 1.467 | —$COO-C_2H_5$ | 6-$CH_3$ | —$N(CH_3)_2$ | O | |
| 1.468 | —$COO-C_3H_7-i$ | 6-$CH_3$ | $CH_3$ | O | |
| 1.469 | —$COO-C_3H_7-i$ | 6-$CH_3$ | $OCH_3$ | O | |
| 1.470 | —$COO-C_3H_7-i$ | 6-$CH_3$ | $OCHF_2$ | O | |
| 1.471 | —$COO-C_3H_7-i$ | 6-$CH_3$ | —$N(CH_3)_2$ | O | |
| 1.472 | —$COOCH_3$ | 6-$CH_3$ | $CH_3$ | S | |
| 1.473 | —$COOCH_3$ | 6-$CH_3$ | $OCH_3$ | S | |
| 1.474 | —$COOCH_3$ | 6-$CH_3$ | $OCHF_2$ | S | |
| 1.475 | —$COOCH_3$ | 6-$CH_3$ | —$N(CH_3)_2$ | S | |
| 1.476 | —$COO-C_3H_7-i$ | 6-$CH_3$ | $CH_3$ | S | |
| 1.477 | —$COO-C_3H_7-i$ | 6-$CH_3$ | $OCH_3$ | S | |

TABLE 1-continued

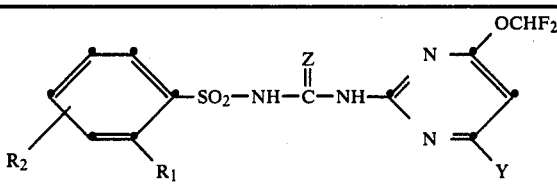

| Compound | R₁ | R₂ | Y | Z | m.p. |
|---|---|---|---|---|---|
| 1.478 | —COO—C₃H₇—i | 6-CH₃ | OCHF₂ | S | |
| 1.479 | —COO—C₃H₇—i | 6-CH₃ | —N(CH₃)₂ | S | |
| 1.480 | —COOCH₃ | 4-NO₂ | CH₃ | O | 186–187° C. |
| 1.481 | —COOCH₃ | 4-No₂ | OCH₃ | O | |
| 1.482 | —COOCH₃ | 4-NO₂ | OCHF₂ | O | |
| 1.483 | —COOCH₃ | 4-NO₂ | —N(CH₃)₂ | O | |
| 1.484 | —COOCH₃ | 4-NH₂ | CH₃ | O | |
| 1.485 | —COOCH₃ | 4-NH₂ | OCH₃ | O | |
| 1.486 | —COOCH₃ | 4-NH₂ | OCHF₂ | O | |
| 1.487 | —COOCH₃ | 4-NH₂ | —N(CH₃)₂ | O | |
| 1.488 | Cl | H | OCH₃ | S | 165–166° C. |
| 1.489 | Cl | H | —N(CH₃)₂ | S | 191° C. (decomp.) |
| 1.490 | —COO—C₃H₇—i | H | Cl | O | 163–166° C. |
| 1.491 | —COO—C₄H₉—s | H | Cl | O | 165–167° C. |

TABLE 2

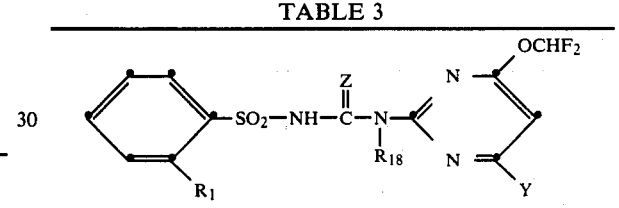

| Compound | R₄ | R₅ | Y | Z | m.p. |
|---|---|---|---|---|---|
| 2.1 | H | H | C₂H₅ | O | |
| 2.2 | H | H | OCH₃ | O | |
| 2.3 | H | H | —N(CH₃)₂ | O | |
| 2.4 | H | Cl | CH₃ | O | 173–174° C. |
| 2.5 | H | Cl | —OCHF₂ | O | |
| 2.6 | H | Cl | OCH₃ | O | |
| 2.7 | H | Cl | C₂H₅ | O | |
| 2.8 | H | H | CH₃ | O | |
| 2.9 | H | H | —OCHF₂ | O | |
| 2.10 | NO₂ | H | CH₃ | O | |
| 2.11 | NO₂ | H | —OCHF₂ | O | |
| 2.12 | NO₂ | H | —N(CH₃)₂ | O | |
| 2.13 | H | —COOCH₃ | —OCHF₂ | O | |
| 2.14 | H | —COOCH₃ | CH₃ | O | |
| 2.15 | H | —SO₂—CH₃ | CH₃ | O | |
| 2.16 | H | —SO₂—CH₃ | —OCHF₂ | O | |
| 2.17 | H | CH₃ | CH₃ | O | |
| 2.18 | H | Cl | —N(CH₃)₂ | O | |
| 2.19 | NO₂ | H | OCH₃ | O | |
| 2.20 | H | —COOCH₃ | OCH₃ | O | |
| 2.21 | H | —COOCH₃ | —N(CH₃)₂ | O | |
| 2.22 | H | —SO₂—CH₃ | OCH₃ | O | |
| 2.23 | H | —SO₂—CH₃ | —N(CH₃)₂ | O | |
| 2.24 | H | CH₃ | OCH₃ | O | |
| 2.25 | H | CH₃ | OCHF₂ | O | |
| 2.26 | H | CH₃ | —N(CH₃)₂ | O | |
| 2.27 | H | OCH₃ | CH₃ | O | |
| 2.28 | H | OCH₃ | OCH₃ | O | |
| 2.29 | H | OCH₃ | OCHF₂ | O | |
| 2.30 | H | OCH₃ | —N(CH₃)₂ | O | |

TABLE 3

| Compound | R₁ | R₁₈ | Y | Z | m.p. |
|---|---|---|---|---|---|
| 3.1 | —COOCH₃ | CH₃ | OCHF₂ | O | 114–115° C. |
| 3.2 | —COOCH₃ | CH₃ | CH₃ | O | |
| 3.3 | —COOCH₃ | CH₃ | OCH₃ | O | |
| 3.4 | —COOCH₃ | CH₃ | —N(CH₃)₂ | O | |
| 3.5 | Cl | CH₃ | CH₃ | O | |
| 3.6 | Cl | CH₃ | OCHF₂ | O | |
| 3.7 | NO₂ | CH₃ | OCHF₂ | O | |
| 3.8 | NO₂ | CH₃ | CH₃ | O | |
| 3.9 | —SO₂—CH₃ | CH₃ | CH₃ | O | |
| 3.10 | —SO₂—CH₃ | CH₃ | OCHF₂ | O | |
| 3.11 | —SO₂—N(CH₃)₂ | CH₃ | CH₃ | O | |
| 3.12 | OCH₃ | CH₃ | OCHF₂ | O | |
| 3.13 | OCH₃ | CH₃ | CH₃ | O | |
| 3.14 | SCH₃ | CH₃ | CH₃ | O | |
| 3.15 | SCH₃ | CH₃ | OCHF₂ | O | |
| 3.16 | NO₂ | CH₃ | OCHF₂ | S | |
| 3.17 | NO₂ | CH₃ | CH₃ | S | |

TABLE 4

| Compound | R₁₉ | Y | m.p. |
|---|---|---|---|
| 4.1 | CH₃ | OCHF₂ | 54–55° C. |
| 4.2 | CH₃ | Cl | |
| 4.3 | CH₃ | OCH₃ | |
| 4.4 | CH₃ | —N(CH₃)₂ | |
| 4.5 | CH₃ | CH₃ | |
| 4.6 | CH₃ | CF₃ | |
| 4.7 | CH₃ | CH₂F | |
| 4.8 | OCH₃ | CH₃ | |
| 4.9 | C₂H₅ | OCHF₂ | |

TABLE 4-continued $$\text{H--N}(R_{19})\text{--}\underset{N}{\overset{N}{\underset{\|}{\diagup}}}\hspace{-2pt}\underset{Y}{\overset{OCHF_2}{\diagdown}}$$

| Compound | $R_{19}$ | Y | m.p. |
|---|---|---|---|
| 4.10 | $C_2H_5$ | Cl | |
| 4.11 | $C_2H_5$ | $OCH_3$ | |
| 4.12 | $C_2H_5$ | $-N(CH_3)_2$ | |
| 4.13 | $C_2H_5$ | $CH_3$ | |
| 4.14 | $C_3H_7-n$ | $CH_3$ | |

TABLE 5

$$R_3\text{--}\underset{R_2}{\overset{}{\diagup}}\hspace{-2pt}\underset{R_1}{\overset{}{\diagdown}}\text{--}SO_2NH\text{--}\overset{Z}{\underset{\|}{C}}\text{--}HN\text{--}\underset{N}{\overset{N}{\diagup}}\hspace{-2pt}\underset{Y}{\overset{OCHF_2}{\diagdown}}$$

| Compound | $R_1$ | $R_2$ | $R_3$ | Y | Z | m.p. |
|---|---|---|---|---|---|---|
| 5.1 | $OCH_3$ | 3-Cl | 5-Cl | $CH_3$ | O | 152–155° |
| 5.2 | $OCH_3$ | 3-Cl | 5-Cl | $OCH_3$ | O | |
| 5.3 | $OCH_3$ | 3-Cl | 5-Cl | $OCHF_2$ | O | |
| 5.4 | $OCH_3$ | 3-Cl | 5-Cl | Cl | O | |
| 5.5 | $OCH_3$ | 3-Cl | 5-Cl | $-N(CH_3)_2$ | O | |
| 5.6 | $CH_3$ | 3-$CH_3$ | 5-$NO_2$ | $CH_3$ | O | 201° C. (decomp.) |
| 5.7 | $CH_3$ | 3-$CH_3$ | 5-$NO_2$ | $OCH_3$ | O | |
| 5.8 | $CH_3$ | 3-$CH_3$ | 5-$NO_2$ | $OCHF_2$ | O | |
| 5.9 | $CH_3$ | 3-$CH_3$ | 5-$NO_2$ | $-N(CH_3)_2$ | O | |
| 5.10 | $OCH_3$ | 3-Cl | 5-Cl | $CH_3$ | S | |
| 5.11 | $CH_3$ | 3-$CH_3$ | 5-$NO_2$ | $OCH_3$ | S | |

FORMULATION EXAMPLES

EXAMPLE 4

Formulation examples for active ingredients of the formula I (throughout, percentages are by weight)

| (a) Wettable powders | (a) | (b) | (c) |
|---|---|---|---|
| active ingredient | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| active ingredient | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether | 4% | 4% |
| (36 moles of ethylene oxide) | | |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| active ingredient | 0.1% | 1% |
| talcum | 99.9% | — |
| kaolin | — | 99% |

Ready-for-use dusts are obtained by mixing the active ingredient with the carriers, and grinding the mixture in a suitable mill.

| (d) Extruder granulate | (a) | (b) |
|---|---|---|
| active ingredient | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| active ingredient | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| active ingredient | 5% |
| isopropylamine | 1% |
| octylphenol polyethylene glycol ether (78 moles of ethylene oxide) | 3% |
| water | 91% |

BIOLOGICAL EXAMPLES

EXAMPLE 5

Preemergence herbicidal activity

Plastic pots are filled with expanded vermiculite (density: 0.135 g/cm³, water absorbing capacity: 0.565 l/l). After the non-absorptive vermiculite has been saturated with an aqueous emulsion in deionised water which contains the test copound in a concentration of 70.8 ppm, seeds of the following plants are sown on the surface: Nasturtium officinalis, Agrostis tenuis, Stellaria media and Digitaria sanguinalis. The pots are then kept in a climatic chamber at 20° C., an illumination of about 20 lux and a relative humidity of 70%. During the germinating phase of 4 to 5 days, the pots are covered with lightpermeable material and watered with deionised water to increase the local humidity. After the 5th day, 0.5% of a commercial liquid fertiliser (Greenzit ®) is added to the water. The test is evaluated 12 days after sowing and the activity on the plants is assessed according to the following rating:

1: plants have not emerged or are totally withered
2-3: very pronounced activity
4-6: medium activity
7-8: weak activity
9: non activity (as untreated controls).

Preemergence activity
Concentration of the test emulsion: 70.8 ppm

| Compound | Nasturtium | Stellaria | Agrostis | Digitaria |
|---|---|---|---|---|
| 1.1 | 2 | 2 | 1 | 1 |
| 1.3 | 1 | 2 | 1 | 2 |
| 1.4 | 1 | 1 | 1 | 1 |
| 1.7 | 2 | 2 | 1 | 2 |
| 1.10 | 2 | 2 | 1 | 1 |
| 1.11 | 1 | 7 | 1 | 9 |
| 1.12 | 2 | 2 | 2 | 2 |
| 1.13 | 1 | 2 | 1 | 2 |
| 1.16 | 1 | 2 | 1 | 2 |
| 1.18 | 2 | 1 | 1 | 1 |
| 1.19 | 1 | 1 | 1 | 1 |
| 1.20 | 1 | 1 | 1 | 1 |
| 1.21 | 1 | 3 | 1 | 1 |
| 1.33 | 1 | 8 | 1 | 8 |
| 1.42 | 1 | 2 | 1 | 2 |
| 1.43 | 1 | 1 | 1 | 1 |
| 1.67 | 1 | 3 | 1 | 2 |
| 1.78 | 2 | 2 | 1 | 2 |
| 1.79 | 3 | 3 | 5 | 2 |
| 1.83 | 1 | 2 | 1 | 2 |
| 1.85 | 1 | 3 | 1 | 2 |
| 1.93 | 1 | 2 | 1 | 2 |
| 1.94 | 1 | 1 | 1 | 1 |
| 1.100 | 2 | 2 | 2 | 2 |
| 1.101 | 2 | 3 | 1 | 3 |
| 1.102 | 1 | 2 | 1 | 2 |
| 1.109 | 1 | 1 | 1 | 1 |
| 1.110 | 2 | 2 | 2 | 2 |
| 1.113 | 2 | 4 | 2 | 3 |
| 1.114 | 2 | 5 | 3 | 7 |
| 1.130 | 1 | 1 | 1 | 1 |
| 1.139 | 2 | 5 | 2 | 7 |
| 1.140 | 2 | 6 | 2 | 1 |
| 1.144 | 3 | 7 | 3 | 3 |
| 1.146 | 1 | 1 | 1 | 1 |
| 1.148 | 2 | 3 | 1 | 3 |
| 1.149 | 1 | 1 | 2 | 2 |
| 1.310 | 1 | 2 | 1 | 2 |
| 1.317 | 1 | 2 | 1 | 1 |
| 1.342 | 2 | 9 | 2 | 8 |
| 1.352 | 2 | 3 | 2 | 3 |
| 1.375 | 1 | 1 | 1 | 1 |
| 1.381 | 1 | 1 | 1 | 1 |
| 1.387 | 3 | 6 | 3 | 6 |
| 1.390 | 1 | 2 | 1 | 2 |
| 1.395 | 2 | 2 | 1 | 4 |
| 1.401 | 1 | 6 | 1 | 6 |
| 2.4 | 2 | 8 | 2 | 8 |
| 3.1 | 1 | 1 | 1 | 1 |
| 5.1 | 2 | 7 | 3 | 9 |

EXAMPLE 6

Test of selectivity in preemergence application

Seeds of dicot and monocot weeds and cultivated plants are sown in a greenhouse in pots of 11 cm diameter. Immediately afterwards the surface of the soil is treated with an aqueous dispersion or solution of the test compound. Concentrations of 0.250, 0.125 and 0.06 kg a.i./ha are employed. The pots are then kept in the greenhouse at 22°–25° C. and 50–70% relative humidity. The test is evaluated after 3 weeks and the activity is determined in accordance with the same rating as in Example 5.

| Activity rate of apln. in kg a.i./ha | Compound 1.1 | | | Compound 1.2. | | | Compound 1.5 | | | Compound 1.18 | | |
|---|---|---|---|---|---|---|---|---|---|---|---|---|
| Test | 0.25 | 0.12 | 0.6 | 0.25 | 0.12 | 0.06 | 0.25 | 0.12 | 0.06 | 0.25 | 0.12 | 0.06 |
| Maize | 2 | 3 | 4 | 8 | 9 | 9 | 4 | 6 | 7 | 3 | 3 | 5 |
| Avena fatua | 2 | 2 | 2 | 2 | 2 | 2 | 3 | 4 | 5 | 3 | 4 | 7 |
| Alopecurus myos. | 2 | 2 | 2 | 2 | 2 | 2 | 2 | 2 | 3 | 3 | 3 | 4 |
| Echinochloa c.g. | 2 | 2 | 3 | 4 | 4 | 4 | 2 | 2 | 4 | 2 | 2 | 2 |
| Cyperus escul. | 1 | 1 | 1 | 1 | 2 | 2 | 2 | 3 | 4 | 3 | 3 | 4 |
| Soybeans | 6 | 7 | 9 | 4 | 5 | 6 | 7 | 9 | 9 | 7 | 7 | 7 |
| Abutilon | 1 | 1 | 3 | 1 | 1 | 1 | 3 | 3 | 3 | 2 | 2 | 3 |
| Xanthium Sp. | 2 | 3 | 4 | 1 | 1 | 2 | 4 | 4 | 8 | 4 | 4 | 4 |
| Chenopodium Sp. | 3 | 3 | 3 | 1 | 2 | 3 | 4 | 4 | 4 | 2 | 2 | 3 |
| Sinapis | 2 | 2 | 2 | 1 | 1 | 1 | 2 | 2 | 2 | 3 | 4 | 4 |
| Stellaria | 3 | 3 | 3 | 2 | 2 | 2 | 3 | 3 | 3 | — | — | — |
| Chrysanthe. leuc. | 2 | 2 | 2 | 2 | 2 | 2 | 2 | 3 | 3 | — | — | — |
| Galium aparine | 2 | 3 | 3 | 2 | 2 | 2 | 2 | 3 | 3 | 3 | 3 | 3 |
| Viola tricolor | 2 | 2 | 2 | 2 | 2 | 2 | 3 | 3 | 3 | 2 | 2 | 2 |

-continued
Test results (preemergence)

| Activity rate of apln. in kg a.i./ha | Compound 1.1 | | | Compound 1.2. | | | Compound 1.5 | | | Compound 1.18 | | |
|---|---|---|---|---|---|---|---|---|---|---|---|---|
| Test | 0.25 | 0.12 | 0.6 | 0.25 | 0.12 | 0.06 | 0.25 | 0.12 | 0.06 | 0.25 | 0.12 | 0.06 |
| Veronica Sp. | 2 | 2 | 2 | 1 | 1 | 1 | 1 | 1 | 1 | — | — | — |

—: not tested.

EXAMPLE 7

Postemergence herbicidal action (contact action)

A number of weeds and cultivated plants, both monocots and dicots, are sprayed postemergence, in the 4- to 6-leaf stage, with an aqueous dispersion of test compound at a rate of application of 0.5 kg a.i./ha, and then kept at 24°–26° C. and 45–60% relative humidity. The test is evaluated 15 days after treatment and the action is assessed in accordance with the same rating as in the preemergence test.

Postemergence activity
Rate of application: 0.5 kg a.i./ha

| Compound | Avena | Setaria | Lolium | Solanum | Sinapis | Stellaria | Phaseolus |
|---|---|---|---|---|---|---|---|
| 1.1 | 3 | 4 | 4 | 4 | 3 | 3 | 7 |
| 1.2 | 3 | 3 | 4 | 3 | 3 | 2 | 3 |
| 1.5 | 5 | 4 | 5 | 3 | 4 | 4 | 7 |

EXAMPLE 8
Growth inhibition of tropical cover crops

The test plants (psophocarpus palustris and centrosema pubescens) are reared until fully grown and then cut back to a height of 15 cm. The plants are sprayed 7 days later with an aqueous emulsion of the compound to be tested. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of new growth in untreated control plants).

EXAMPLE 9
Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of the formula I until thoroughly wetted. The concentration of test compound is up to 100 g a.i./ha. Evaluation is made about 5 weeks after application. Compared with untreated controls, the compounds of the formula I markedly increase the number and weight of the harvested siliques on the leading shoot.

| Compound | Rate of application g/ha | Siliques on the leading shoot compared with controls (in %) | |
|---|---|---|---|
| | | number | weight |
| 1.1 | 3 | 110 | 112 |
| | 10 | 120 | 118 |
| | 30 | 110 | 112 |
| controls | 0 | 100 | 100 |

EXAMPLE 10
Growth inhibition of cereals

Summar barley (Hordeum vulgare) and summer rye (Secale) are sown in sterilised soil in plastic beakers in a greenhouse and watered as required. The cereal shoots are treated about 21 days after sowing with an aqueous spray mixture of a compound of the formula I. The concentration corresponds to 0.5 and 2.5 kg respectively of active ingredient per hectare. Evaluation of the growth of the cereals is made 10 and 21 days after application. Compared with untreated controls, the new growth of the treated plants is markedly reduced and in some plants the diameter of the stalks is increased.

| | New growth (growth in height) in % compared with controls | |
|---|---|---|
| Compound | barley 50 g a.i./ha | rye 50 g a.i./ha |
| 1.1 | — | 60 |
| 1.2 | 0 | — |
| 1.3 | 100 | 85 |
| 1.4 | 70 | 85 |
| 1.5 | 60 | — |
| 1.18 | 50 | 70 |
| 1.102 | 15 | 90 |
| controls | 100 | 100 |

—: not tested.

EXAMPLE 11
Growth inhibition of grasses

A mixture of the grasses Lolium perenne, Poa pratensis, Festuca ovina, Dactylis glomerata and Cynodon dactylon is sown in plastic dishes filled with an earth/peat/sand mixture (6:3:1), in a greenhouse, and watered as required. The emergent grasses are cut back weekly to a height of 4 cm above the soil and, 50 days after sowing and 1 day after the last cut, are sprayed with an aqueous spray mixture of compound of the formula I. The concentration of test compound corresponds to a rate of application of 100 kg per hectare. The growth of the grasses is assessed after 21 days. Compared with untreated controls, the new growth of plants treated with compounds of formula I is markedly reduced.

| Compound | New growth (growth in height) in % compared with controls mixtures of grasses 50 g a.i./ha |
|---|---|
| 1.1 | 16 |
| 1.2 | 15 |
| 1.3 | 65 |
| 1.4 | 15 |
| 1.5 | 60 |
| 1.18 | 40 |
| 1.102 | 10 |
| controls | 100 |

What is claimed is:

1. An N-arylsulfonyl-N'-pyrimidinyl urea of the general formula I

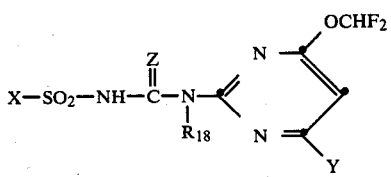

wherein
X is a radical of the formula

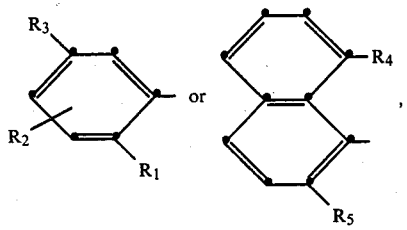

Y is $C_1$-$C_3$alkyl, $C_1$-$C_3$haloalkyl, $C_1$-$C_3$alkoxy, $C_1$-$C_3$haloalkoxy, $C_2$-$C_3$alkoxyalkyl, $C_1$-$C_3$alkylthio, halogen or $-NR_{16}R_{17}$, Z is oxygen or sulfur, $R_1$ is hydrogen, halogen, cyano, nitro, $C_1$-$C_4$haloalkyl, $C_1$-$C_4$alkyl, $C_1$-$C_4$alkoxy, $-CO-R_6$, $-NR_7R_8$, $-S(O)_m-C_1$-$C_4$alkyl or $-SO_2R_9$, $R_2$ is hydrogen, fluorine, chlorine, bromine, nitro, trifluoromethyl, $-NR_{20}R_{21}$, methyl, ethyl, methoxy, ethoxy or $-S(O)_mZ-C_1$-$C_4$alkyl, $R_3$ is hydrogen, fluorine, chlorine, bromine, amino, nitro or methoxy, $R_6$ is hydrogen, $C_1$-$C_4$alkyl, $C_3$-$C_5$alkenyloxy, $C_3$-$C_5$alkynyloxy, $C_1$-$C_4$haloalkyl, $C_1$-$C_5$alkylthio, phenoxy, benzyloxy, $-NR_{10}R_{11}$ or $C_1$-$C_5$alkoxy which is unsubstituted or substituted by 1 to 3 halogen atoms or $C_1$-$C_3$alkoxy, $R_7$ is hydrogen, methoxy, ethoxy, $C_1$-$C_4$alkyl or $-CO-R_{12}$, $R_8$ is hydrogen or $C_1$-$C_4$alkyl, $R_9$ is an $-O-R_{13}$ or $-NR_{14}R_{15}$ group, $R_{13}$ is $C_1$-$C_4$alkyl which is unsubstituted or substituted by 1 to 3 halogen atoms, or is phenyl or benzyl, $R_{18}$ is hydrogen, $C_1$-$C_3$alkyl or $C_1$-$C_3$alkoxy, and m is 0, 1 or 2, and $R_4$ has the same meaning as $R_2$; $R_5$ has the same meaning as $R_1$; $R_{10}$, $R_{11}$, $R_{14}$ and $R_{20}$ have each the same meaning as $R_7$; and $R_{12}$, $R_{15}$, $R_{16}$, $R_{17}$ and $R_{21}$ have each the same meaning as $R_8$, or a salt thereof.

2. A compound according to claim 1, wherein X is the unsubstituted or substituted phenyl radical.

3. A compound according to claim 1, wherein Y is a radical containing at most 2 carbon atoms.

4. A compound according to claim 1, wherein Z is oxygen.

5. A compound according to claim 1, wherein $R_3$ and $R_4$ are hydrogen.

6. A compound according to claim 1, wherein $R_{18}$ is hydrogen or methyl.

7. A compound according to claim 1, wherein X is the unsubstituted or substituted phenyl radical, Y is a radical containing at most 2 carbon atoms, Z is oxygen and $R_3$ and $R_{18}$ are hydrogen.

8. A compound according to claim 7, wherein $R_2$ is hydrogen.

9. A compound according to claim 1, wherein X is the unsubstituted or substituted phenyl nucleus, Y is a radical containing at most 2 carbon atoms, Z is oxygen and $R_{18}$ is hydrogen, and wherein $R_1$ is hydrogen, halogen, nitro, $C_1$-$C_4$haloalkyl, $C_1$-$C_4$alkoxy, $C_1$-$C_4$alkyl, $-S(O)_m-C_1$-$C_4$alkyl, $-SO_2-N(CH_3)_2$, $-SO-OCH_2CF_3$ or $-CO-R_6$; $R_2$ is hydrogen, fluorine, chlorine, nitro, amino, trifluoromethyl, methyl, methoxy, ethoxy or $-S(O)_m-C_1$-$C_4$alkyl; $R_6$ is hydrogen, methyl, $C_3$-$C_5$alkenyloxy, $C_3$-$C_5$alkynyloxy, $C_1$-$C_3$alkylthio, dimethylamino, methylamino, amino or $C_1$-$C_5$alkoxy which is unsubstituted or substituted by 1 to 3 halogen atoms or $C_1$-$C_3$alkoxy; and m is 0, 1 or 2.

10. N-(2-Chlorophenylsulfonyl)-N'-(4-difluoromethoxy-6-methylpyrimidin-2-yl)urea according to claim 1.

11. N-(2-Methoxycarbonylphenylsulfonyl)-N'-[4,6-bis-(difluoromethoxy)pyrimidin-2-yl]urea according to claim 1.

12. N-(2-Methoxycarbonylphenylsulfonyl)-N'-(4-difluoromethoxy-6-methylpyrimidin-2-yl)urea according to claim 1.

13. N-(2-Methoxycarbonylphenylsulfonyl)-N'-(4-difluoromethoxy-6-methoxypyrimidin-2-yl)urea according to claim 1.

14. N-(2-Nitrophenylsulfonyl)-N'-(4-difluoromethoxy-6-methylpyrimidin-2-yl)urea according to claim 1.

15. A herbicidal and growth-regulating composition which comprises an effective amount of at least one compound according to claim 1, together with a suitable carrier therefor.

16. A method of controlling undesired plant growth, which method comprises applying thereto or to the locus thereof a herbicidally effective amount of a compound according to claim 1.

17. A method of regulating plant growth, which method comprises applying thereto or to the locus thereof an effective amount of a compound according to claim 1.

18. A method of regulating plant growth in order to achieve greater yields, which method comprises applying thereto or the locus thereof an effective amount of a compound according to claim 1.

19. A method according to claim 16 for selectively controlling weeds in crops of cultivated plants which method comprises applying the compound according to claim 1 preemergence or postemergence.

20. A method according to claim 19 for controlling weeds in crops of sugar cane, maize and cotton.

21. A method according to claim 19 for controlling weeds in crops of soybeans.

22. A method according to claim 19 for controlling perennial weeds in crops of cultivated plants.

23. A method according to claim 17, for suppressing plant growth beyond the two-leaf stage which method comprises applying the compound according to claim 1 preemergence.

24. A method according to claim 18 for regulating plant growth in crops of soybeans.

25. A method according to claim 17 for suppressing the growth of cover crop leguminosae.

* * * * *